United States Patent [19]

Chan

[11] 4,412,992

[45] Nov. 1, 1983

[54] 2-HYDROXY-5-PHENYLAZOBENZOIC ACID DERIVATIVES AND METHOD OF TREATING ULCERATIVE COLITIS THEREWITH

[75] Inventor: Rosalind P. K. Chan, London, England

[73] Assignee: Biorex Laboratories Limited, England

[21] Appl. No.: 281,504

[22] Filed: Jul. 8, 1981

[30] Foreign Application Priority Data

Jul. 21, 1980 [GB] United Kingdom ............... 8023826

[51] Int. Cl.$^3$ ............... A61K 31/655; C07C 107/06
[52] U.S. Cl. ............................ 424/226; 260/207
[58] Field of Search ...................... 260/207; 424/226

[56] References Cited

U.S. PATENT DOCUMENTS 3,915,951 10/1975 Agback et al. ............... 260/207
4,045,429 8/1977 Agback ........................ 260/207

OTHER PUBLICATIONS

*Chemical Abstracts*, vol. 88, p. 53, abstract No. 69263x, 1978.

*Primary Examiner*—Alvin E. Tanenholtz
*Assistant Examiner*—Frederick W. Pepper
*Attorney, Agent, or Firm*—Wenderoth, Lind & Ponack

[57] ABSTRACT

The present invention provides a pharmaceutical composition for treating ulcerative colitis containing at least one compound of the general formula:

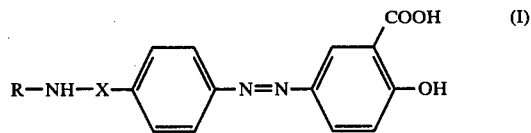

wherein X is an $-SO_2-$ or $-CO-$ group and R is either an unsubstituted or substituted non-heterocyclic aromatic ring system or is a radical of the general formula $-(CH_2)_n-Y$, in which Y is a hydroxyl group, an unsubstituted or substituted amino group or a carboxylic or sulphonic acid group and n is a whole number of from 1 to 6 and in which one or more hydrogen atoms in the alkylene radical can be replaced by unsubstituted or substituted amino groups or alkyl radicals and in which the $-(CH_2)_n-Y$ radical is either attached directly to the nitrogen atom or via a benzene ring; and/or containing at least one ester thereof and/or at least one non-toxic, pharmaceutically acceptable salt thereof, in admixture with a solid or liquid pharmaceutical diluent or carrier. Furthermore, the present invention provides a process for preparing the compounds of the above-given general formulae and also provides a method of treating ulcerative colitis.

13 Claims, No Drawings

2-HYDROXY-5-PHENYLAZOBENZOIC ACID DERIVATIVES AND METHOD OF TREATING ULCERATIVE COLITIS THEREWITH

BACKGROUND OF THE INVENTION

Ulcerative colitis is a disease of increasing prevalence for which at present the only satisfactory treatment is the administration of salazopyrin, which has the following structural formula:

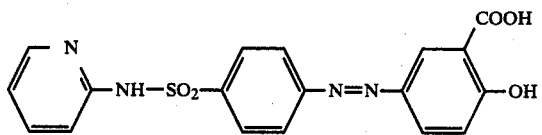

However, one serious disadvantage of salazopyrin is that it is broken down in the intestinal tract to give sulphaphyridine which gives rise to undesirable side effects. Furthermore, salazopyrin is insoluble in water.

We have now found that when the pyridylsulphamoyl moiety of salazopyrin is replaced by certain non-heterocyclic organic radicals, compounds are obtained which are very useful for the treatment of ulcerative colitis and have the great advantage that breakdown thereof in the intestinal tract does not give rise to undesirable metabolic products. Furthermore, many of them are soluble in water, which is advantageous for ease of administration, and have a very low acute toxicity.

SUMMARY OF THE INVENTION

Thus, according to the present invention, there are provided pharmaceutical compositions containing at least one compound of the general formula:

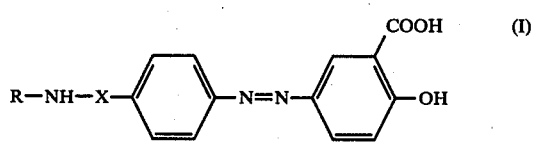

wherein X is an —SO$_2$— or —CO— group and R is either an unsubstituted or substituted non-heterocyclic aromatic ring system and preferably a benzene ring or is a radical of the general formula —(CH$_2$)$_n$—Y, in which Y is a hydroxyl group, an unsubstituted or substituted amino group or a carboxylic or sulphonic acid group and n is a whole number of from 1 to 6 and in which one or more hydrogen atoms in the alkylene radical can be replaced by unsubstituted or substituted amino groups or alkyl radicals, and in which the —(CH$_2$)$_n$—Y radical is either attached directly to the nitrogen atom or via a benzene ring; and/or containing at least one ester thereof and/or at least one non-toxic, pharmaceutically acceptable salt thereof, in admixture with a solid or liquid pharmaceutically diluent or carrier.

Most of the compounds of general formula (I) are new. Consequently, the present invention also provides new compounds of the general formula:

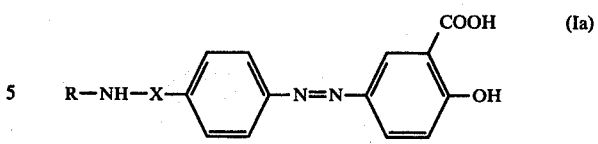

wherein X is an —SO$_2$— or —CO— group and R is either an unsubstituted or substituted non-heterocyclic aromatic ring system and preferably a benzene ring or is a radical of the general formula —(CH$_2$)$_n$—Y, in which Y is a hydroxyl group or an unsubstituted or substituted amino group or a carboxylic or sulphonic acid group and n is a whole number of from 1 to 6 and in which one or more of the hydrogen atoms in the alkylene radical can be replaced by unsubstituted or substituted amino groups or alkyl radicals, and in which the —(CH$_2$)$_n$—Y radical is either attached directly to the nitrogen atom or via a benzene ring, with the proviso that RNHX is other than a —CO—NH—CH$_2$—COOH radical; and the esters and the non-toxic, pharmacologically acceptable salts thereof, for example the salts with alkali metals and alkaline earth metals or with non-toxic amines.

DETAILED DESCRIPTION OF THE INVENTION

Substituted amino groups present in the compounds according to the present invention are preferably mono- or dialkylamino radicals, the alkyl moieties of which contain up to 6 and preferably up to 3 carbon atoms, methyl and ethyl being especially preferred.

The compounds of general formula (I) can be prepared by diazotising an amine of the general formula:

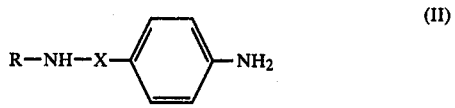

in which R and X have the same meaning as above, followed by coupling with salicyclic acid, whereafter, if desired, the compound obtained is salified with a non-toxic inorganic or organic base.

The following Examples are given for the purpose of illustrating the present invention:

EXAMPLE 1

(a) A mixture of 100 g. N-acetylsulphanilyl chloride, 80 g. aniline sulphate and 80 g. sodium carbonate in 500 ml. acetone was heated under reflux while stirring, for 5 hours, cooled and then added to a mixture of dilute hydrochloric acid and ice. The precipitate obtained was filtered off, washed with water and diethyl ether and dried in a vacuum at 50° C. to give 110 g. of almost pure N-acetylsulphanilylanilide; m.p. 212°–215° C.

(b) 100 g. N-Acetylsulphanilylanilide was heated under reflux for 3 hours in 150 ml. aqueous hydrochloric acid (1:1 v/v). After cooling, the reaction mixture was diluted with water and further cooled to 0° C. The 90 g. of sulphanilylanilide hydrochloride which deposited were filtered off, washed with ice-cold water and recrystallised from ethanol; m.p. 191°–193.5° C.

(c) 10 g. Sulphanilylanilide hydrochloride and 10 ml. concentrated hydrochloric acid in 600 ml. ethanol were gently warmed to dissolve, then cooled to 5° C. and treated dropwise with 30 ml. of a 10% aqueous solution of sodium nitrite. The reaction mixture was left to stand for 1 hour at 0° to 5° C. and then filtered. While maintaining the temperature at 0° to 5° C., the filtrate was added dropwise to a solution of 5 g. salicylic acid in 100 ml. of an aqueous solution containing 4 g. sodium carbonate and 7 g. sodium hydroxide cooled to 0° C. The reaction mixture was left to stand for 3 hours at 0° C. and at ambient temperature for 20 hours, while maintaining a pH of >8, whereafter it was concentrated on a rotavapor apparatus and acidified. The gummy precipitate obtained was separated off and boiled with water several times to remove excess salicylic acid. The residue was dissolved in diethyl ether and the ethereal solution was washed with water, dried over anhydrous sodium sulphate and treated with charcoal. After filtering and removing the diethyl ether, the crude product obtained was dissolved in the minimum amount of acetone and ten times the volume of diethyl ether added thereto. Upon cooling, there were obtained 3.5 g. 5-(4-phenylsulphamoylphenylazo)-salicylic acid; m.p. 232°–234° C.

(d) 11 g. 5-(4-Phenylsulphamoylphenylazo)-salicyclic acid in 100 ml. ethanol were treated with an ethanolic solution of an equivalent amount of sodium hydroxide. The resulting solution was concentrated to a small volume at 30° C. and 20 mm.Hg, whereafter an equal volume of diethyl ether was added to the concentrate. Upon cooling, sodium 5-(4-phenylsulphamoylphenylazo)-salicylate deposited, which was filtered off, washed with diethyl ether and petroleum ether (b.p. 40°–60° C.) and dried at 50° C. in a vacuum; m.p. 257°–259° C. The yield was 12 g.

EXAMPLE 2

(a) A solution of 22 g. 4-aminohippuric acid in 20 ml. hydrochloric acid and 200 ml. water was cooled to 0° C. and treated dropwise, while stirring, with 80 ml. of a 10% aqueous solution of sodium nitrite. The reaction mixture was then stirred for 1 hour, whereafter a solution of 14 g. salicylic acid in 150 ml. 2 N aqueous sodium hydroxide solution containing 15 g. sodium carbonate and cooled to 0° C. was added dropwise thereto. The reaction mixture was left to stand overnight at ambient temperature and then poured into a mixture of ice and dilute hydrochloric acid. The fine precipitate obtained was extracted with boiling ethyl acetate and the solution treated with charcoal. After filtering, the filtrate was evaporated to remove the solvent and the residue was crystallised from boiling ethanol to give 30 g. 5-(4-carboxymethylcarbamoylphenylazo)-salicylic acid; m.p. 260°–262° C.

(b) A solution of 11 g. 5-(4-carboxymethylcarbamoylphenylazo)-salicylic acid in 500 ml. warm ethanol was treated with an ethanolic solution containing two equivalents of sodium hydroxide and the deposit obtained was filtered off, washed with ethanol and diethyl ether and dried in a vacuum at 50° C. There were obtained 12.5 g. of the disodium salt 5-(4-carboxymethylcarbamoylphenylazo)-salicylic acid; m.p. >360° C.

EXAMPLE 3

9.71 g. Aminohippuric acid were dissolved in a mixture of 40 ml. 2.5 N hydrochloric acid and 10 ml. 2.5 N sulphuric acid and 50 g. ice added thereto. A solution of 3.5 g. sodium nitrite in 15 ml. water were added steadily at 0° C., the reaction mixture being well stirred during the addition. After 75 minutes at 0° C., the reaction mixture was added to a solution of 6.9 g. salicylic acid in 37 ml. of a mixture of 9 parts by volume of 5 N aqueous sodium hydroxide solution and 1 part by volume of 5 N aqueous sodium carbonate solution, the temperature being kept at 0° C. by the addition of ice.

After 15 minutes, 23 ml. of a mixture of 4 parts by volume of 5 N hydrochloric acid and 1 part by volume of 5 N acetic acid was slowly added, while stirring. The precipitate obtained was filtered off, washed with distilled water and dried in a vacuum at 80° C. to give 17.2 g. (100% of theory) 5-(4-carboxymethylcarbamoylphenylazo)-salicylic acid, which can be recrystallised from 80% acetic acid, aqueous acetone or aqueous dimethylformamide to give a yellow, crystalline product of at least 99% purity in a yield of 80 to 95%; m.p. 260°–262° C.

EXAMPLE 4

(a) 125 g. Finely powdered 4-nitrobenzoyl chloride were added portionwise, while stirring, to a solution of 70 g. β-alanine in 500 ml. water containing 65 g. sodium hydroxide and cooled to 5° C. The reaction mixture was stirred for 3 hours and then added to a mixture of ice and hydrochloric acid. The precipitate obtained was filtered off, washed with water and dried by suction. After crystallisation of the dried product from hot acetone, there were obtained 130 g. 4-nitrobenzoyl-β-alanine; m.p. 164°–166° C.

(b) A suspension of 15 g. finely powdered 4-nitrobenzoyl-β-alanine in 200 ml. ethanol was stirred in an atmosphere of hydrogen in the presence of 1 g. of palladium-charcoal (5%), while cooling gently. When the absorption of hydrogen had ceased, the reaction mixture was filtered and the filtrate concentrated to a small volume. Upon adding diethyl ether and cooling, 4-aminobenzoyl-β-alanine was obtained. The yield was 11.5 g.; m.p. 156°–158° C.

(c) 8.8 g. 4-Aminobenzoyl-β-alanine were triturated with 12 ml. hydrochloric acid and the paste obtained was dissolved in 100 ml. water. The solution was cooled to −5° C. and a solution of 3 g. sodium nitrite in 20 ml. water, cooled to 0° C., was added dropwise, while stirring. The diazotised solution was left for 1 hour at 0° C. and was then added dropwise at −5° C. to a solution of 6 g. salicylic acid in 70 ml. water containing 3.6 g. sodium hydroxide and 7 g. sodium carbonate. The final reaction mixture was adjusted to a pH of about 8, stirred for 2 to 3 hours and added to a mixture of dilute hydrochloric acid and ice. The precipitate obtained was filtered off, washed with water and suction dried. Crystallisation from hot ethanol gave 11.9 g. 5-(carboxyethylcarbamoyl-4-phenylazo)-salicylic acid; m.p. 254°–255° C.

10.7 g. of the free acid were dissolved in 300 ml. warm ethanol and treated with a solution of 2.4 g. sodium hydroxide in 25 ml. ethanol. The precipitate obtained was filtered off, washed with ethanol and diethyl ether and dried in a vacuum at 50° C. to give 11.5 g. of the disodium salt of 5-(carboxyethylcarbamoyl-4-phenylazo)-salicylic acid; m.p. >350° C.

EXAMPLE 5

(a) 20 g. Finely powdered 4-nitrobenzoyl chloride were added portionwise to 12.5 g. taurine in a solution of 8 g. sodium hydroxide in 50 ml. water. The reaction mixture was stirred for 3 hours and then acidified. Precipitated 4-nitrobenzoic acid was filtered off and the filtrate distilled to dryness at a pressure of 15 mm.Hg. The residue was extracted with boiling ethanol and the extract then cooled to give a yield of 23.6 g. 4-nitrobenzoyltaurine; m.p. 278°–280° C.

(b) A solution of 17 g. 4-nitrobenzoyltaurine in 100 ml. water was stirred in an atmosphere of hydrogen in the presence of 1 g. palladium-charcoal (5%) until the absorption of hydrogen ceased. The reaction mixture was then filtered, the filtrate was mixed with 20 ml. hydrochloric acid and the suspension of the hydrochloride obtained cooled to −5° C. This was added dropwise, while stirring, to a solution of 5 g. sodium nitrite in 30 ml. water. The diazotised solution thus obtained was stirred for 30 minutes and then added to 9.5 g. salicylic acid in a solution of 11 g. sodium hydroxide in 100 ml. water, cooled to −2° C. The mixture was stirred for 3 hours, poured into a mixture of ice and 15 ml. hydrochloric acid and stirred at 0° C. for 30 minutes. The precipitate obtained was filtered off and washed with ice-cold water. Crystallisation from 20% aqueous ethanol gave 18.2 g. 5-(sulphoethylcarbamoyl-4-phenylazo)-salicylic acid; m.p. >350° C. (decomp.).

EXAMPLE 6

(a) A solution of 10 ml. ethanolamine in 120 ml. 10% aqueous sodium hydroxide solution was cooled to 5° C. and 30 g. finely powdered 4-nitrobenzoyl chloride added thereto portionwise. The reaction mixture was stirred for 24 hours and filtered. The solid obtained, which mainly consisted of bis-(4-nitrobenzoyl)-ethanolamine, was hydrolysed with 200 ml. of 4% aqueous ethanolic sodium hydroxide at ambient temperature for 24 hours. The reaction mixture was added to the above filtrate, acidified and the precipitated 4-nitrobenzoic acid was filtered off. The filtrate was concentrated and the 13 g. of precipitated N-4-nitrobenzoylethanolamine isolated. The mother liquor was distilled to dryness and the residue was boiled with ethanol. Concentration of the ethanolic extract gave a further 5.3 g. of product; m.p. 134°–135° C.

(b) A solution of 21 g. of N-4-nitrobenzoylethanolamine in 400 ml. ethanol was stirred in an atmosphere of hydrogen in the presence of 1 g. palladium-charcoal (5%) until the absorption of hydrogen had ceased. The catalyst was filtered off and the ethanolic solution was evaporated to dryness to give a thick oil which slowly solidified. Thin layer chromatography showed that the N-4-aminobenzoylethanolamine thus obtained had a purity of more than 99%: it was used as such for the next stage of the synthesis.

(c) A solution of 16 g. N-4-aminobenzoylethanolamine in 20 ml. hydrochloric acid and 150 ml. water was cooled to −5° C. and treated dropwise, while stirring, with a solution of 7 g. sodium nitrite in 50 ml. water. The reaction mixture was further stirred for 1 hour and then added dropwise to 120 ml. of 10% aqueous sodium hydroxide solution containing 13 g. salicylic acid and cooled to −2° C. The reaction mixture was stirred for 3 hours and the precipitate obtained filtered off, washed with ice-cold water, suction dried and crystallised from hot ethanol to give 11 g. sodium 5-(4-hydroxyethylcarbamoylphenylazo)-salicylate; m.p. 286°–288° C. (decomp.).

The filtrate from which the sodium salt had been removed was acidified. The precipitate obtained was filtered off, washed with water, suction dried, charcoaled in ethyl acetate-methanol (2:1 v/v) and concentrated to give 2.7 g. 5-(4-hydroxyethylcarbamoyl-phenylazo)-salicylic acid which was identical in all respects to the free acid regenerated from the sodium salt; m.p. 225°–226° C. (decomp.).

EXAMPLE 7

(a) A solution of 7 g. alanine in 65 ml. of 10% aqueous sodium hydroxide solution was treated portionwise, while stirring, with 12.5 g. finely powdered 4-nitrobenzoyl chloride. The reaction mixture was stirred at 5° C. for 20 hours, acidified and the precipitate isolated, washed with water and suction dried. Repeated fractional crystallisation from acetone-diethyl ether (2:1 v/v) gave 4-nitrobenzoylalanine; m.p. 199°–200° C.

(b) 2 g. 4-Nitrobenzoylalanine in 50 ml. ethanol were hydrogenated in the presence of 0.2 g. palladium-charcoal (5%). Removal of the catalyst and of the solvent gave a solid which was crystallised from ethanol-diethyl ether (1:2 v/v) to give 4-aminobenzoylalanine; m.p. 198°–199° C.

(c) A solution of 0.8 g. 4-aminobenzoyl chloride in 15 ml. 1 N hydrochloric acid was cooled to −5° C. and diazotised with 5 ml. of 10% aqueous sodium nitrite solution for 30 minutes. The reaction mixture was then added to a solution of 0.7 g. salicylic acid in 15 ml. of water containing 0.8 g. sodium hydroxide and 0.5 g. sodium carbonate. After 2 hours, the reaction mixture was acidified and the precipitate obtained was isolated, dissolved in ethyl acetate and the solution was washed, dried and charcoaled. The solution was then concentrated and cooled to give 0.9 g. 5-($\alpha$-methylcarboxymethylcarbamoyl-4-phenylazo)-salicylic acid; m.p. 252°–254° C.

EXAMPLE 8

(a) 20 g. Acetylsulphanilyl chloride were added portionwise at 5° C., with stirring, to a solution of 15 g. 4-aminophenylacetic acid in 10% aqueous sodium hydroxide solution. The reaction mixture was further stirred for 4 hours and then added to a mixture of dilute hydrochloric acid and ice. The precipitate obtained was isolated, taken up in ethyl acetate, washed with water, dried and evaporated to give 22 g. acetylsulphanilyl-4-(carboxymethyl)-anilide.

(b) 3.5 g. Acetylsulphanilyl-4-(carboxymethyl)-anilide in 7 ml. 5 N hydrochloric acid were heated under reflux for 2 hours, cooled, diluted with 20 ml. ice and water and cooled to −5° C. 8 ml. of 10% aqueous sodium nitrite solution were added thereto and after 30 minutes the diazotised solution was added to 1.4 g. salicylic acid in 20 ml. of an aqueous solution of 2 g. sodium hydroxide and 2 g. sodium carbonate cooled to below 0° C. The reaction mixture was stirred for 2 hours and then added to a mixture of hydrochloric acid and ice. The precipitate obtained was isolated and dissolved in ethyl acetate and the solution washed with water, dried and charcoaled. Upon concentrating the filtered solution and adding an equal volume of diethyl ether to the filtrate, the desired product slowly crystallised out. There were obtained 3 g. 5-[(4-carboxymethyl;phenyl)-sulphamoyl-4-phenylazo]-salicylic acid; m.p. 252°–254° C.

EXAMPLE 9

(a) A solution of 12 g. 6-aminohexanoic acid in 60 ml. of 10% aqueous sodium hydroxide solution was treated portionwise with 9 g. finely powdered 4-nitrobenzoyl chloride. After 4 hours, the reaction mixture was added to a mixture of dilute hydrochloric acid and ice. The precipitate obtained was isolated, washed with water and crystallised from acetone to give 12.6 g. (4-nitrobenzoyl)-6-aminohexanoic acid; m.p. 148°–150° C.

(b) A solution of 6 g. (4-nitrobenzoyl)-6-aminohexanoic acid in 150 ml. ethanol was hydrogenated in the presence of 0.5 g. palladium-charcoal (5%) until the reaction was complete. The catalyst and solvent were removed and the residue was crystallised from ethanol-diethyl ether (1:1 v/v) to give 4.7 g. (4-aminobenzoyl)-6-aminohexanoic acid; m.p. 132°–134° C.

(c) A solution of 2.5 g. (4-aminobenzoyl)-6-aminohexanoic acid in 15 ml. 2 N hydrochloric acid was cooled to −5° C. and treated dropwise, while stirring, with 8 ml. of a 10% aqueous solution of sodium nitrite. The reaction mixture was stirred for 30 minutes and then added at −5° C. to salicylic acid in 20 ml. of water containing 2 g. sodium hydroxide and 1 g. sodium carbonate. After 3 hours, the reaction mixture was acidified and the precipitate obtained was isolated by centrifuging, dissolved in ethyl acetate, washed, dried and concentrated to a small volume. Upon cooling, there were obtained 2.7 g. 5-(carboxypentylcarbamoyl-4-phenylazo)-salicylic acid; m.p. 238°–239° C.

EXAMPLE 10

(a) A solution of 13 g. copper sulphate in 60 ml. water and a solution of 2 g. sodium hydroxide in 30 ml. water were added simultaneously to a solution of 7.5 g. lysine in 50 ml. water, followed by the addition of 50 ml. of 10% aqueous sodium bicarbonate solution. The precipitated salt was filtered off and the blue filtrate was added, with vigorous stirring, to a solution of 7 g. 4-nitrobenzoyl chloride in 50 ml. acetone. The reaction mixture was stirred for 20 hours and the precipitate obtained was filtered off, washed with water, methanol and diethyl ether and dried in a vacuum at 50° C. to give the copper salt of δ-(4-nitrobenzoyl)-lysine.

(b) A suspension of 7 g. of the copper salt of δ-(4-nitrobenzoyl)-lysine in 30 ml. water was stirred with 6 ml. hydrochloric acid until dissolution was complete. Hydrogen sulphide was passed in for 1 hour and precipitated copper sulphide then filtered off. The filtrate was evaporated to dryness and the residue was taken up in 20 ml. methanolic hydrogen chloride and heated under reflux for 3 hours. The cooled reaction mixture was diluted with water, rendered alkaline with sodium carbonate and extracted with ethyl acetate to give 4.8 g. δ-(4-nitrobenzoyl)-lysine methyl ester in the form of a yellow oil.

(c) A solution of 1 g. δ-(4-nitrobenzoyl)-lysine methyl ester in 2 ml. methyl iodide and 0.2 ml. acetone was left to stand for 20 hours at ambient temperature, whereafter the NMR showed the reaction to be complete. The volatile materials were evaporated off to leave δ-(4-nitrobenzoyl)-α,α-dimethyl-lysine methyl ester in the form of an oil.

(d) 1 g. δ-(4-nitrobenzoyl)-α,α-dimethyllysine methyl ester in 20 ml. ethanol was hydrogenated in the presence of 0.1 g. palladium-charcoal (5%) until the absorption of hydrogen had ceased. The catalyst was filtered off and the filtrate evaporated to dryness. The residue was taken up in 5 ml. 2 N hydrochloric acid, cooled to −5° C. and treated with 2.5 ml. of 10% aqueous sodium nitrite solution. After standing for 30 minutes, the clear solution was added at −5° C. to a solution of 0.5 g. salicylic acid in 20 ml. of a 1 N aqueous sodium hydroxide solution. After subsequently standing for 3 hours at 20° C., the reaction mixture was acidified and extracted with diethyl ether to remove unreacted salicylic acid. The aqueous phase was adjusted to pH 7 by adding 1 N aqueous sodium hydroxide solution and the resulting solution was evaporated to dryness. The residue was further dried by adding toluene and subsequently evaporating it and the residue then extracted with methanol. The methanolic solution was concentrated to a small volume. After adding diethyl ether and cooling, the disodium salt of 5-(α-dimethylaminocarboxypentylcarbamoyl-4-phenylazo)-salicylic acid separated out; m.p. >210° C. (decomp.).

EXAMPLE 11

(a) A solution of 30 ml. N,N-diethylethylenediamine in 100 ml. water was treated portionwise, while stirring, with 15 g. finely powdered 4-nitrobenzoyl chloride. The reaction mixture was stirred for 20 hours and the precipitate obtained was filtered off, washed with water and aqueous sodium carbonate solution and crystallised from petroleum ether-diethyl ether (1:1 v/v) to give 6 g. N,N-diethyl-(4-nitrobenzoyl)-ethylenediamine; m.p. 49°–51° C.

(b) A solution of 5 g. N,N-diethyl-(4-nitrobenzoyl)-ethylenediamine in 40 ml. ethanol was hydrogenated in the presence of 0.3 g. palladium-charcoal (5%) until the reaction was complete. The catalyst and solvent were removed to give 5 g. N,N-diethyl-(4-aminobenzoyl)-ethylenediamine in the form of an oil.

(c) A solution of 2.35 g. N,N-diethyl-(4-aminobenzoyl)-ethylenediamine in 20 ml. 2 N hydrochloric acid was cooled to −5° C. and treated with 8 ml. of a 10% aqueous solution of sodium nitrite. The reaction mixture was stirred for 30 minutes and added to 1.4 g. salicylic acid in a solution of 1.6 g. sodium hydroxide and 2 g. sodium carbonate in 20 ml. water. After 3 hours at 0° to 20° C., sodium chloride was added to the reaction mixture to salt out the desired diazo compound. This was filtered off, washed with water and hot methanol and dried to give 2.3 g. 5-(diethylaminoethylcarbamoyl-4-phenylazo)-salicylic acid; m.p. 252°–254° C. (decomp.).

The pharmaceutical compositions according to the present invention contain at least one of the compounds (I) in admixture with a solid or liquid pharmaceutical carrier.

Solid compositions for oral administration include compressed tablets, pills, dispersible powders and granules. In such solid compositions, one of the compounds (I) is admixed with at least one inert diluent, such as calcium carbonate, starch, alginic acid or lactose. The compositions may also comprise, as is normal practice, additional substances other than inert diluents, for example, lubricating agents, such as magnesium stearate.

Liquid compositions for oral administration include pharmaceutically acceptable emulsions, solutions, suspensions, syrups and elixirs containing inert diluents commonly used in the art, such as water and liquid paraffin. Besides inert diluents, such compositions may also comprise adjuvants, such as wetting and suspension agents, and sweetening and flavouring agents.

The compositions according to the present invention for oral administration, include capsules of absorbable material, such as gelatine, containing at least one of the compounds (I), with or without the addition of diluents or excipients.

The percentage of active material in the compositions of the present invention may be varied, it being necessary that it should constitute a proportion such that a suitable dosage for the desired therapeutic effect shall be obtained. In general, the preparations of the present invention should be administered orally or parenterally to humans to give 500 to 5000 mg. and preferably 500 to 2000 mg. of active substance per day.

The following Examples illustrate pharmaceutical compositions according to the present invention:

EXAMPLE 12

| 600 mg. tablets are prepared containing: | |
|---|---|
| disodium salt of 5-(carboxyethyl-carbamoyl-4-phenylazo)-salicylic acid | 500 mg. |
| starch | 50 mg. |
| lactose | 45 mg. |
| magnesium stearate | 5 mg. |

EXAMPLE 13

| 450 mg. tablets are prepared containing: | |
|---|---|
| sodium 5-(4-carboxymethylcarbamoyl-phenylazo)-salicylate | 250 mg. |
| starch | 100 mg. |
| lactose | 95 mg. |
| magnesium stearate | 5 mg. |

The tablets according to Examples 12 and 13 are intended for administration to humans for the treatment of ulcerative colitis.

An attempt was made to establish an acute oral toxicity profile for the disodium salts of 5-(4-carboxymethyl-carbamoylphenylazo)-salicylic acid and of 5-(carboxyethylcarbamoyl-4-phenylazo)-salicylic acid, using rats and mice as experimental animals but this was not possible due to their low toxicity. No deaths were observed with the carboxymethyl compound when administered to mice at a dosage of 3 g./kg. and to rats at a dosage of 2 g./kg. and no deaths were observed with the carboxyethyl compound when administered to mice at a dosage of 4 g./kg. and to rats at a dosage of 2 g./kg.

Experiments have also been carried out on groups of 6 male Wistar rats in order to ascertain whether the new compounds according to the present invention split in the same manner as sulphasalazine to liberate 5-aminosalicylic acid (5-ASA). The test compounds were administered in an amount of 45 to 50 mg./kg. The results obtained are set out in the following Table:

| | % of dose measured as 5-ASA | | |
|---|---|---|---|
| test compound | faeces | urine | total |
| sulphasalazine | 26 ± 4 | 17 ± 2 | 43 ± 4 |
| Example 1 | 24 ± 3 | 19 ± 3 | 43 ± 3 |
| Example 2 | 17 ± 3 | 17 ± 6 | 34 ± 5 |
| Example 4 | 22 ± 2 | 14 ± 2 | 36 ± 3 |
| Example 5 | 26 ± 3 | 15 ± 2 | 41 ± 5 |
| Example 6 | 22 ± 2 | 19 ± 3 | 41 ± 4 |

The above results clearly demonstrate that the new compounds of the present invention split in the same manner as sulphasalazine and can be expected to exert at least as beneficial an effect as sulphasalazine but without the disadvantage of giving rise to other compounds which exert undesirable side effects, such as the sulphapyridine formed from sulphasalazine.

I claim:

1. 2-Hydroxy-5-phenylazobenzoic acid derivatives of the general formula:

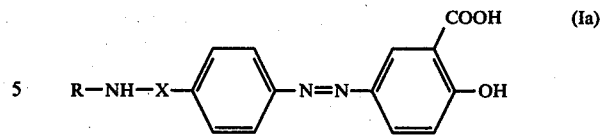

wherein X is an $-SO_2-$ or $-CO-$ group and R is either a phenyl or carboxymethylphenyl radical or is a radical of the formula $-(CH_2)_n-Y$, in which Y is a hydroxyl group, an amino group, a monoalkyl- or dialkyl-amino group, the alkyl moieties of which contain up to 6 carbon atoms or a carboxylic or sulphonic acid group and n is a whole number of from 1 to 6 and in which one or more of the hydrogen atoms in the alkylene radical can be replaced by amino groups, monoalkyl- or dialkyl-amino groups, the alkyl moieties of which contain up to 6 carbon atoms or alkyl radicals and in which the $-(CH_2)_n-Y$ radical is either attached directly to the nitrogen atom or via a benzene ring, with the proviso that $R-NH-X-$ is other than a $-CO-NH-CH_2-COOH$ radical; and the esters and non-toxic, pharmacologically acceptable salts thereof.

2. 5-(4-Phenylsulphamoylphenylazo)-salicylic acid and the sodium salt thereof.

3. Disodium salt of 5-(4-carboxymethylcarbamoyl-phenylazo)-salicylic acid.

4. 5-(Carboxyethylcarbamoyl-4-phenylazo)-salicylic acid and the disodium salt thereof.

5. 5-(Sulphoethylcarbamoyl-4-phenylazo)-salicylic acid.

6. 5-(4-Hydroxyethylcarbamoylphenylazo)-salicylic acid and the sodium salt thereof.

7. 5-($\alpha$-Methylcarboxymethylcarbamoyl-4-phenylazo)-salicylic acid.

8. 5-[(4-Carboxymethylphenyl)-sulphamoyl-4-phenylazo]-salicylic acid.

9. 5-(Carboxypentylcarbamoyl-4-phenylazo)-salicylic acid.

10. 5-($\alpha$-Dimethylaminocarboxypentylcarbamoyl-4-phenylazo)-salicylic acid and the disodium salt thereof.

11. 5-(Diethylaminoethylcarbamoyl-4-phenylazo)-salicylic acid.

12. A pharmaceutical composition for the treatment of ulcerative colitis in humans, containing an effective amount to treat ulcerative colitis, of at least one compound of the formula:

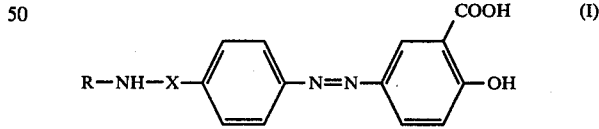

wherein X is an $-SO_2-$ or $-CO-$ group and R is either phenyl or carboxymethylphenyl radical or is a radical of the general formula $-(CH_2)_n-Y$, in which Y is a hydroxyl group, an amino group or a monoalkyl- or dialkyl-amino group, the alkyl moieties of which contain up to 6 carbon atoms or a carboxylic or sulphonic acid group and n is a whole number of from 1 to 6 and in which one or more hydrogen atoms in the alkylene radical can be replaced by amino groups, monoalkyl- or dialkyl-amino groups, the alkyl moieties of which contain up to 6 carbon atoms or alkyl radicals and in which the $-(CH_2)_n-Y$ radical is either attached directly to the nitrogen atom or via a benzene ring; and/or containing at least one ester thereof and/or at least one nontoxic, pharmaceutically acceptable salt thereof, in admixture with a solid or liquid pharmaceutical diluent or carrier.

13. A method of treating ulcerative colitis in a human, wherein a compound of the formula given in claim 12, optionally in admixture with a solid or liquid pharmaceutical diluent or carrier, is administered orally to a human suffering from ulcerative colitis in a daily dosage of from 500 to 5000 mg.

* * * * *